(12) United States Patent
Pedersen et al.

(10) Patent No.: US 6,646,744 B2
(45) Date of Patent: Nov. 11, 2003

(54) COUPLING ELEMENTS FOR SURFACE PLASMON RESONANCE SENSORS

(75) Inventors: Henrik Chresten Pedersen, Jyllinge (DK); Carsten Thirstrup, Charlottenlund (DK)

(73) Assignee: Vir A/S, Taastrup (DK)

( * ) Notice: Subject to any disclaimer, the term of this patent is extended or adjusted under 35 U.S.C. 154(b) by 132 days.

(21) Appl. No.: 09/908,651

(22) Filed: Jul. 20, 2001

(65) Prior Publication Data

US 2002/0044285 A1 Apr. 18, 2002

Related U.S. Application Data

(60) Provisional application No. 60/219,663, filed on Jul. 21, 2000.

(51) Int. Cl.[7] .......................... G01N 21/55; H01J 40/14
(52) U.S. Cl. .................................. 356/445; 250/237 G
(58) Field of Search ................................ 356/445, 305, 356/600, 601; 250/227.24, 237 R, 237 G

(56) References Cited

U.S. PATENT DOCUMENTS

| 4,696,536 A | | 9/1987 | Albares et al. | |
|---|---|---|---|---|
| 4,752,130 A | | 6/1988 | George et al. | |
| 5,313,264 A | | 5/1994 | Ivarsson et al. | |
| 5,482,800 A | | 1/1996 | Gal | |
| 5,492,840 A | * | 2/1996 | Malmqvist et al. | 356/318 |
| 6,466,323 B1 | * | 10/2002 | Anderson et al. | 356/445 |

FOREIGN PATENT DOCUMENTS

| EP | 0 797 090 A2 | 9/1997 |
|---|---|---|
| EP | 0 863 395 A2 | 9/1998 |
| WO | WO 00/46589 | 8/2000 |

OTHER PUBLICATIONS

Behrmann et al., "Excimer laser micromachining for rapid fabrication of diffractive optical elements," Applied Optics, vol. 36, No. 20, pp. 4666–4674, Jul. 10, 1997.

Breidne et al., "Blazed holographic gratings," Optica Acta, vol. 26, No. 11, 1427–1441, 1979.

Budzinski et al., "Radiation resistant gratings and their optical properties," Optik, vol. 87, No. 3, pp. 121–125, 1991.

Champagne, "Nonparaxial Imaging, Magnification, and Aberration Properties in Holography," Journal of the Optical Society of America, vol. 57, No. 1, pp. 51–55, Jan. 1967.

Jacobs et al., "Liquid crystal optics," Optic News, pp. 39–40, Dec. 1989.

(List continued on next page.)

*Primary Examiner*—Kevin Pyo
(74) *Attorney, Agent, or Firm*—Birch, Stewart, Kolasch & Birch, LLP

(57) ABSTRACT

The present invention provides configurations and a method of formation of optical coupling elements for surface plasmon resonance sensors. In the method of the present invention, interference patterns between two overlapping monochromatic coherent light beams are created on a photosensitive film disposed on a master substrate. At least one of the light beams has an oblique angle of incidence onto the master substrate, and the focal points of the two overlapping light beams are positioned in order to reduce optical aberrations up to third order. After developing the photosensitive film, the surface relief patterns pattern created on the master substrate is replicated as diffractive optical element onto SPR sensor chips. The diffractive optical elements working as optical coupling elements diffract an incoming light beam into an oblique angle within the range from 40 to ~80 degrees.

24 Claims, 12 Drawing Sheets

OTHER PUBLICATIONS

Figure 1:
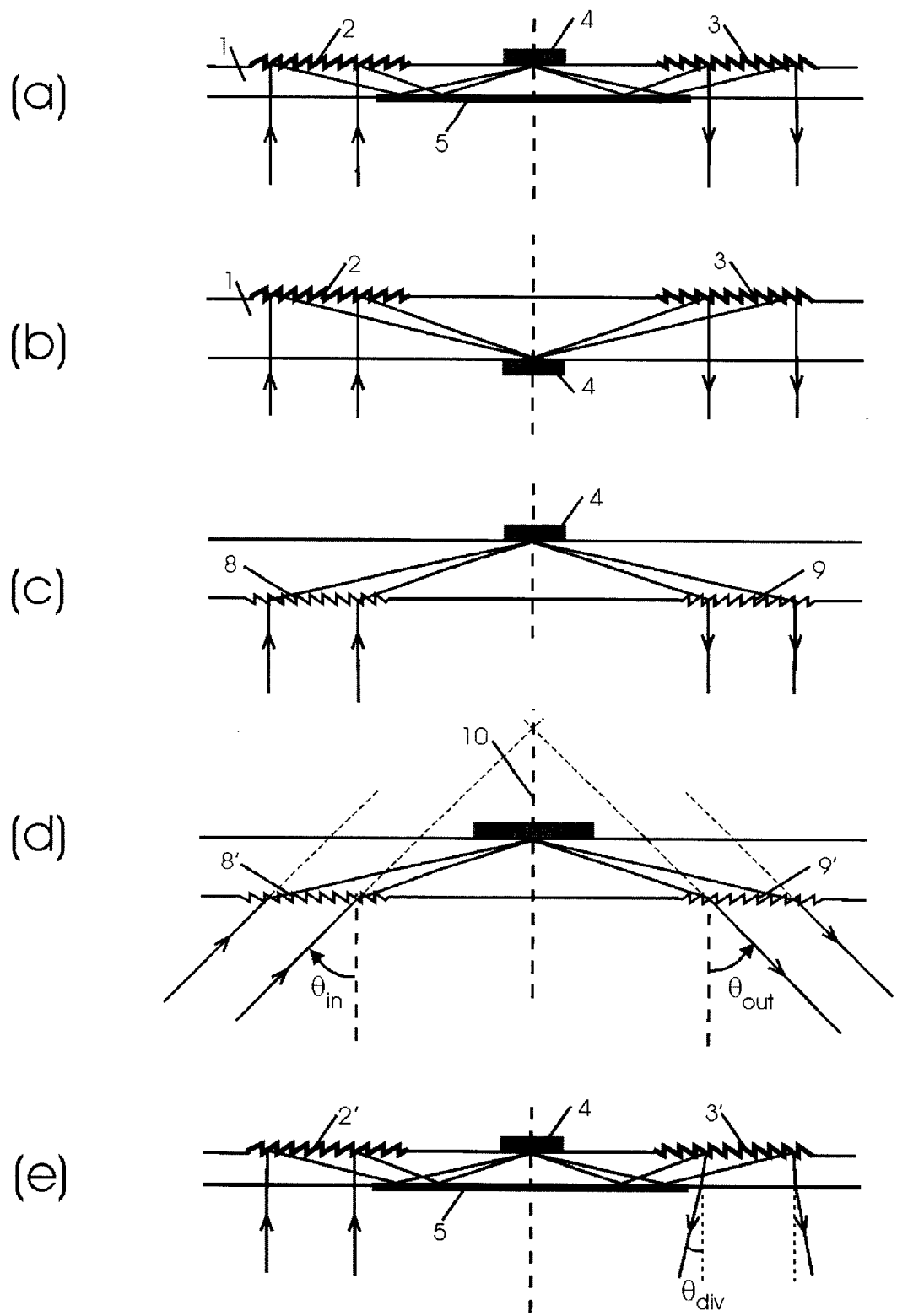

Kley, "E-beam lithography: a suitable technology for fabrication of high-accuracy 2D and 3D surface profiles," SPIE, vol. 2640, pp. 71–80.

Latta, "Computer-Based Analysis of Hologram Imagery and Aberrations. I. Hologram Types and Their Nonchromatic Aberrations," Applied Optics, vol. 10, No. 3, pp. 599–618, Mar. 1971.

Lesem et al., "The Kinoform: A New Wavefront Reconstruction Device," IBM J. Res. Develop., pp. 150–155, Mar. 1969.

Mansell et al., "Binary-optic smoothing with isotropic etching," Applied Optics, vol. 26, No. 20, pp. 4644–4647, Jul. 10, 1997.

Miler et al., "Holographic diffractive collimators based on recording with homocentric diverging beams for diode lasers," Applied Optics, vol. 38, No. 14, pp. 3019–3024, May 10, 1999.

Popov et al., "Technological problems in holographic recording of plane gratings," Optical Engineering, vol. 31, No. 10, pp. 2168–2173, Oct. 1992.

Reimer et al., "Fabrication of Microrelief Surfaces using a One-Step Lithography Process," Proc. SPIE vol. 3226 Microelectronic Structures and MEMS for Optical Processing III, Austin, 1997; pp. 1–9.

Sheridon, "Production of Blazed Holograms," Applied Physics Letters, vol. 12, No. 9, pp. 316–318, May 1, 1968.

Futhey et al., "Superzone diffractive lenses," 1992 OSA Technical Digest Series, vol. 9, pp. 4–6.

* cited by examiner

COUPLING ELEMENTS FOR SURFACE PLASMON RESONANCE SENSORS

This application claims priority on provisional Application No. 60/219,663 filed on Jul. 21, 2000, the entire contents of which are hereby incorporated by reference.

The present invention relates to the formation and manufacturing of diffractive optical input and output grating couplers in surface plasmon resonance (SPR) sensor chips. The SPR sensor chips are being employed in optical bio-/chemical sensor systems, where the function of the SPR sensor chips is to measure bio-/chemical compounds in liquids or in gasses.

In surface plasmon resonance (SPR) sensors, it is important to have an efficient and reliable coupling without critical alignment between the following three components: 1) the light source (LS); 2) the sensing domain (SD), and 3) the optical detector (OD). The SD is defined as the region where interaction between the light and the surface plasmon occurs. It comprises an SPR metal film (typically a few tenths of nanometers) and a superstrate of one or more bio-/chemically active sensing areas. The optical coupling between the LS and the SD can be defined as the input coupling (IC) and the optical coupling between the SD and the optical detector can be defined as the output coupling (OC).

SPR sensors can be divided into three main concepts (A, B and C) according to the integration between the 5 components as defined above, LS, SD, OD, IC and OC. A is the discrete concept, where all 5 components are separated mechanically and the IC and the OC are achieved by means of optical components such as lenses, mirrors, optical fibres, and filters or diffractive optical elements (DOEs). B is the sensor chip concept, where the OD and the IC and OC are integrated in an SPR sensor chip and the optoelectronic components LS and OD are either discrete components and may be mounted on the same electrical circuit board, or they may be integrated on the same optoelectronic chip. C is the integrated optics sensor concept, where all 5 components are integrated on the same chip.

Concept A has traditionally dominated the commercial market of SPR sensors (e.g. products such as BIAcore and IBIS). The disadvantages of concept A are large, bulky and expensive systems, which usually require substantial service. For bio-/chemical sensors, concept C has attracted a great deal of interest within the last 20 years. Typically, an SPR sensor based on this concept consists of optical waveguides as ICs and OCs directing the light from an integrated LS to the SD disposed in a microchannel, and an integrated OD detects the output light beam. Although it is rather a hybrid solution than full integrated one, Texas Instruments has approached this concept and have commercialised an SPR system marketed under the name Spreeta, where all components are integrated in the same housing—see EP 0 797 090. The Spreeta system has a fairly low production cost, but the disadvantages are an unhandy housing and the fact that the user has to dispose all optical and electro-optical components, when replacing the bio-/chemistry on the SD.

The present invention relates to concept B and it has the advantages of the user friendliness of A and the simple optics and low price of C. In fact, since only the sensor chip is being replaced, the production costs can be very low. The present invention is an oblique angle holographic method of formation of ICs and OCs as diffraction gratings integrated on an SPR sensor chip. The formation of ICs and OCs as diffraction gratings is being made in such a manner that the coupling between the LS, the SD and the OD can be established without critical alignment. This enables the light to be accurately directed to the SD with an appropriate angle, focal length and focal point size. The present oblique angle holographic method is particularly suitable for formation of diffraction gratings that have large diffraction angles, as high as ~80° from the plane of incidence.

For SPR sensing, the angle of incident light to the SPR film is lying in the range 40° to 80°. One method to couple light into an SPR sensor chip is using a high index prism and an index matching gel (U.S. Pat. No. 5,313,264). In the present invention, where index-matching gels are eliminated, diffraction gratings employed as ICs and OCs are disposed onto an SPR sensor chip.

For an SPR sensor chip with mutually parallel flat topside surface and flat backside surface, the diffraction condition that light rays from each grating spacing of the diffraction grating interfere constructively yields the following expression for the grating spacing $a_p$ of the p'th grating element;

$$a_p = \frac{m\lambda}{n_g x_p} y_i \left[ 1 + \left(\frac{x_p}{y_i}\right)^2 \right]^{1/2}, \quad (1)$$

where $\lambda$ is the wavelength of light, m is the diffract on order, $x_p$ and $y_i$ are the horizontal and vertical distances between the focal point of the diffraction grating and the position of the p'th grating element with p=0 being the first element and p=N being the last element in the grating. In case of one or more reflection points (M) of light between the p'th grating element and the focal point of the diffraction grating, $y_i$ has to be multiplied by M+1.

For SPR sensing, the large angle of incidence of the light beam puts high requirements to the accuracy of the formation of the diffraction gratings. This is evident from the following example, where we assume that the input light beam has a wavelength of 670 nm, the substrate of the SPR sensor chip has a refractive index of 1.65 (e.g. a polymer substrate with high refractive index), and the SD comprises an SPR gold film with a superstrate on the top having a refractive index of 1.46 (e.g. a polymer membrane for ion-detection). As a result, the SPR angle is ~73°. In order to cover this angle in the angle span of the input light beam, the SPR sensor chip may have the following dimensions: $y_i$=2 mm, $x_{p=0}$=8 mm and $x_{p=N}$=5 mm resulting in an aperture of 3 mm. Assuming a diffraction order of m=1, eqn. (1) yields $a_0$=418 nm and $a_N$=437 nm. The number of grating periods is ~7050 and the difference in the grating spacing between two neighbouring grating elements is ~$(a_N-a_0)$}/7050=0.003 nm. For maximum diffraction efficiency, the depths of the gratings (d) are approximately ~100 nm for reflection gratings and ~800 nm for transmission gratings.

In practice, it would be acceptable to divide the aperture into sections of grating elements with a fixed periodicity in each section. Dividing the full aperture into 100 sections of grating elements, the minimum difference in the grating spacing from one section to the neighbouring section can then be increased to 0.3 nm. However, it is noted that for m=1, the requirement, of the method of formation of the diffraction grating are still very severe.

Alternatively, one can increase the diffraction order m, and the dimensions of the diffraction gratings scale accordingly. On the other hand, by choosing a large value of m, e.g. m>10, it becomes more difficult to optimise the performance of the diffraction grating. There is therefore a need in the art of a method, which accurately forms diffraction gratings on SPR sensor chips working in low order diffraction modes, m<10.

There are numerous methods of formation of diffraction gratings. The gratings are either directly fabricated on a substrate, e.g. glass or they are made in a mould, and the structure in the mould is subsequently transferred to another substrate, usually a transparent plastic like acrylics or polycarbonate. There are mechanical methods like single-point diamond turning [P. P. Clark, and C. Londoño, Opt. News 15, p. 39–40 (1989)], where a diamond tool with a radius as small as a few micrometers is translated incrementally to grind the desired grating profile into the substrate. A more coarse mechanical method is plunge-cut diamond turning [J. Futhey and M. Fleming, *Superzone diffractive lenses*, Vol. 9 of 1992 OSA Technical Digest Series, pp. 4–6], where a diamond with a triangular or trapezoidal profile is rotated and transfers the profile to the substrate. The groove dimensions with these methods are limited to the micron range and are most suitable for spherically symmetric structures.

There are scanning analogue writing methods like variable-energy e-beam lithography [E.-B. Kley and B. Schnabel, Proc. SPIE 2640, pp.71–80 (1995)], and laser micromaching [G. P. Behrmann and M. T. Duignan, Appl. Optics 36, pp.4666–4674], where a focussed laser beam writes directly onto the substrate itself or a photoresist. There are phase-only computer generated holograms also known as kinoforms [L. B. Lesem, P. M. Hirsch, and J. A. Jordan Jr., IBM J. Res. Develop. 13, pp.150–155 (1969)], which are fabricated by printing a large-format grey-scale of the desired phase and photoreducing the print into emulsion, which is subsequently developed to generate the desired phase object. Lithographic methods and kinoforms are very flexible methods and they can generate arbitrary diffraction gratings. The draw-back of these methods is the fact that they rely on scanning a lithographic tool with a resolution of typically 50 nm–1000 nm and a positioning accuracy over a large area. With the requirements for the diffraction gratings as mentioned above, the resolutions achievable are not sufficient.

For fabrication of gratings, there are multimasks photolithographic methods [J. D. Mansell, D. R. Neal, and S. W. Smith, Appl. Optics: 36, pp.4644–4647 (1997)] typically with four levels of mask layers to form a binary optic structure as an approximation to the grating profile. There are single masks analogue methods like grey-tone photolithography [U.S. Pat. No. 5,482,800 (Jan. 9, 1996)], where a large array of black spots on a mask creates a desirable diffraction pattern, which under UV exposure generates the desired grating profile on the photoresist. The advantages with the photolithographic methods are that the whole structure is exposed in a short time and thermal drift effects are small. The resolution of photolithographic methods is usually limited to >20 nm, which also is not sufficiently low for the requirements of the diffraction gratings mentioned above.

Interferometric methods based on producing interference fringes from standing waves [N. K. Sheridan Appl. Phys. Left. 12, pp.316–318 (1968)], transmission fringes from a Fabry-Perot interferometer or from superimposition of a Fourier series of sinusoidal patterns of appropriate amplitude and phase [M. Breidne, S. Johansson, L.-E. Nilson, and H. Ahlen, Opt. Acta 26, 1427 (1979)] have also been reported. Technologically, these methods are difficult and they are limited to particular shapes of diffractive structures.

Analogue holographic recording methods are based on creating an interference pattern on a photosensitive film on a substrate from two beams originating from the same laser [E. B. Champagne, J. Opt. Soc. An. 57, 51 (1967); J. Latta, Appl. Opt. 10, 599 (1971); M. Miler, I. Koudela, and I. Aubrecht, Appl. Opt. 38, pp.3019–3024 (1999)].

The method of the present invention is based on an analogue holographic method, where at least one of the light beams has an oblique angle of incidence onto the substrate and where the interference pattern is transferred to an SPR sensor chip. In addition, the light beams are focussed by means of focussing optics such as lenses and overlap in such a way as to create a light interference pattern on a photosensitive film such as a photoresist; and after developing the photoresist, a surface relief pattern is created and it is transferred to an SPR sensor chip to form an IC. An input light beam incident on the IC is directed and focussed towards the SD at angles covering the SPR angle. Similarly, using the method of the present invention an OC of the SPR sensor chip can be created.

The method of the present invention further includes a procedure of positioning the focal points of the two overlapping light beams in order to reduce optical aberrations up to third order.

In contrast to other methods of forming diffraction gratings, the method of the present invention meets the requirements of accuracy of the formation of the IC and OC of the SPR sensor as mentioned above.

It is an object of the present invention to provide a method of formation of a diffraction grating on an SPR sensor chip as an input optical coupler, which directs and focuses an input light beam onto a sensing domain at an oblique angle defined as an angle larger than 40°.

It is a further object of the present invention to provide a method of formation of a diffraction grating on an SPR sensor chip as an output optical coupler, which directs and collimates the light beam reflected from the sensing domain to an optical detector.

It is a still further object of the present invention to provide a method of formation of diffraction gratings, where the diffraction grating images a light source with a known angular energy distribution onto a predefined pattern on one surface of an SPR sensor chip.

It is a still further object of the present invention to provide a method of formation of diffraction gratings, where the minimum difference in grating spacing between two grating elements of the diffraction grating is in the nanometer range and even in the subnanometer range.

It is a still further object of the present invention to provide a method of formation of diffraction gratings, where the diffraction grating is created rapidly to avoid excessive effects of thermal instabilities in the recording process.

It is a still further object of the present invention to provide a method of formation of diffraction gratings, where no mechanical scanning is needed that inherently could increase the inaccuracies of the formation of diffraction grating.

It is a still further object of the present invention to provide a method of formation of diffraction gratings by positioning the focal points of the two laser beams at positions such that aberrations are reduced up to third order.

In a first aspect, the present invention relates to a method of forming a first surface relief pattern adapted to be replicated onto a substantially plane surface of a substantially transparent member to form a first diffractive optical element, said substantially transparent member being adapted to form part of a surface plasmon resonance sensor, the method comprising the steps of p1 providing a master substrate, said master substrate having a substantially plane surface, providing a photosensitive layer of material onto the substantially plane surface of the master substrate, exposing the photosensitive layer to a first and a second wave of electromagnetic radiation so as to expose the photosensitive layer to a first interference pattern generated by a spatial overlap at an intersection between the first and second waves of electromagnetic radiation, wherein the first wave of electromagnetic radiation, at the position of the photosensitive layer, has a first mean propagation vector, and wherein the second wave of electromagnetic radiation, at the position of the photosensitive layer, has a second mean propagation vector, the second mean propagation vector forming an angle to the first mean propagation vector at the intersection between the first an second wave of electromagnetic radiation, wherein the angle between the first and second mean propagation vectors is selected so as to change direction of propagation of an incoming wave of electromagnetic radiation having an incoming mean propagation vector in such a way that the smallest angle between the incoming mean propagation vector and a diffracted mean propagation vector is larger than 40 degrees when said incoming wave of electromagnetic radiation is incident upon the first diffractive optical element replicated in the substantially plane surface of the substantially transparent member.

Preferably, the method according to the first aspect of the present invention further comprises the steps of rotating the master substrate approximately 180 degrees around a normal to the surface holding the photosensitive layer, forming a second surface relief pattern on the substantially plane surface of the master substrate by exposing the photosensitive layer to the first and second waves of electromagnetic radiation so as to expose the photosensitive layer to a second interference pattern generated by the spatial overlap at the intersection between the first and second waves of electromagnetic radiation, wherein the first wave of electromagnetic radiation, at the position of the photosensitive layer, has a first mean propagation vector, and wherein the second wave of electromagnetic radiation, at the position of the photosensitive layer, has a second mean propagation vector, the second mean propagation vector forming an angle to the first mean propagation vector at the intersection between the first and second wave of electromagnetic radiation, wherein the angle between the first and second m an propagation vectors is selected so as to change direction of propagation of an incoming wave of electromagnetic radiation having an incoming mean propagation vector in such a way that the smallest angle between the incoming mean propagation vector and a diffracted mean propagation vector is larger than 40 degrees when said incoming wave of electromagnetic radiation is incident upon replication of the second surface relief pattern replicated in the substantially plane surface of the substantially transparent member as a second diffactive optical element.

In most practical situations, the first and second waves of electromagnetic radiation have substantially the same wavelength. In fact, the first and second waves of electromagnetic radiation may be emitted by a same light source, which may comprise a laser source, such as a HeCd laser, a Kr-laser, an excimer laser, or a semiconductor laser. The first, second and the incoming waves of electromagnetic radiation are characterized as object wave, reference wave, and reconstruction waves, respectively.

The method according to the first aspect may further comprise the step of developing the photosensitive layer.

The master substrate itself may constitute the substantially transparent member so that the photosensitive layer is provided directly onto the substantially transparent member—e.g. by spin coating. In this situation the method may further comprise the step of performing a sacrificial-layer-etch of the photosensitive layer in order to replicate the first and said second surface relief pattern(s) into the substantially plane surface of a substantially transparent member. The step of performing a sacrificial-layer-etch of the photosensitive layer may be achieved by means of ion-milling, chemically assisted ion-beam etching or reactive ion etching.

In case the substantially transparent member does not constitute the master substrate, the method according to the first aspect of the present invention may further comprise the step of forming a negative metal master of the first and second surface relief patterns for further replication of said first and second surface relief patterns. Preferably, the metal master is a nickel master.

Further replication may be achieved by replicating the first and second surface relief patterns from the negative metal master using hot embossing. Alternatively, further replication may be achieved by replicating the first and second surface relief patterns from the negative metal master using injection moulding. As a final alternative, the further replication may be achieved by replicating the first and second surface relief patterns from the negative metal master using injection compression moulding. A metal layer may be provided on top of the diffractive optical element(s) replicated from the surface relies pattern(s). Suitable materials are aluminium, gold, silver or the like.

When applying the method according to the first aspect of the present invention, a focal point of the first wave of electromagnetic radiation and a focal point of the second wave of electromagnetic radiation are positioned according to the following procedure expanding to third order in x the expression of a recording grating spacing defined as, $$a_{record}(x) = \frac{\lambda_{record}}{\sin(\theta_1) + \sin(\theta_2)},$$

where x is a direction perpendicular to the lines of the interference pattern, $\lambda_{record}$ is a recording wavelength, $\theta_1$ is the angle of incidence of the first wave of electromagnetic radiation and $\theta_2$ is the angle of incidence of the second wave of electromagnetic radiation, expanding to third order in x the expression of reconstruction grating spacing defined as, $$a_{read}(x) = \frac{\lambda_{read}}{n_g(\sin(\theta_0) - \sin(\theta_i))}.$$

where $\lambda_{read}$ is a reconstruction vacuum wavelength, $n_g$ is a refractive index of the substantially transparent member, $\theta_i$ is the angle of incidence of the incoming wave of electromagnetic radiation and $\theta_0$ is a diffraction angle of a diffracted wave of electromagnetic radiation, and minimizing the expression $$a_{record}(x) - a_{read}(x) = A_0 + A_1(x - x_{centre}) + A_2(x - x_{centre})^2 + A_3(x - x_{centre})^3,$$

with respect to the position of the focal point of the first wave of electromagnetic radiation and the position of the focal point of the second wave of electromagnetic radiation, where $x_{centre}$ is the centre position of the interference pattern, and $A_0$, $A_1$, $A_2$, and $A_3$ are the differences between the first, second, third and fourth expansion coefficients of $a_{record}(x)$ and $a_{read}(x)$, respectively.

In a second aspect, the present invention relates to a coupling element for surface plasmon resonance sensors, said coupling element comprising a diffractive optical element comprising a grating structure having a monotonically increasing spacing in a predetermined direction, the diffractive optical element being adapted to diffract an incoming wave of electromagnetic radiation having a first mean propagation vector into a diffracted wave of electromagnetic radiation having a second mean propagation vector, wherein the diffractive optical element forms part of a surface of a solid and substantially transparent member, and wherein the direction of propagation defined by the second mean propagation vector is different from the direction of propagation defined by the first mean propagation vector in such a way that the smallest angle between the first and second mean propagation vectors is larger than 40 degrees.

The grating structure may form a transmission grating structure or, alternatively, a reflection grating structure. The diffractive optical element may be adapted to focus an incoming wave of electromagnetic radiation. Alternatively, the diffractive optical element may be adapted to collimate a diverging wave of electromagnetic radiation.

The diffractive optical element may further comprise one or more calibration marks, said one or more calibration marks being areas with missing grating structures.

The invention will now be explained in further details with reference to the accompanying figures.

FIG. 1 Schematics of cross-sectional views of 5 different configurations of diffraction gratings on SPR sensor chips as formed by the method of the present invention. In FIGS. 1(a–c), the input light beams and the output light beams are collimated with normal incidence. In FIG. 1(d), the input light beam is collimated with an angle of incidence ($\theta_{in}$) different from zero and the output light beam is collimated with an output angle ($\theta_{out}$) different from zero. In FIG. 1(e), the input light beam is collimated with normal incidence and the output light beam is diverging with a divergence angle ($\theta_{div}$).

Figure 2:
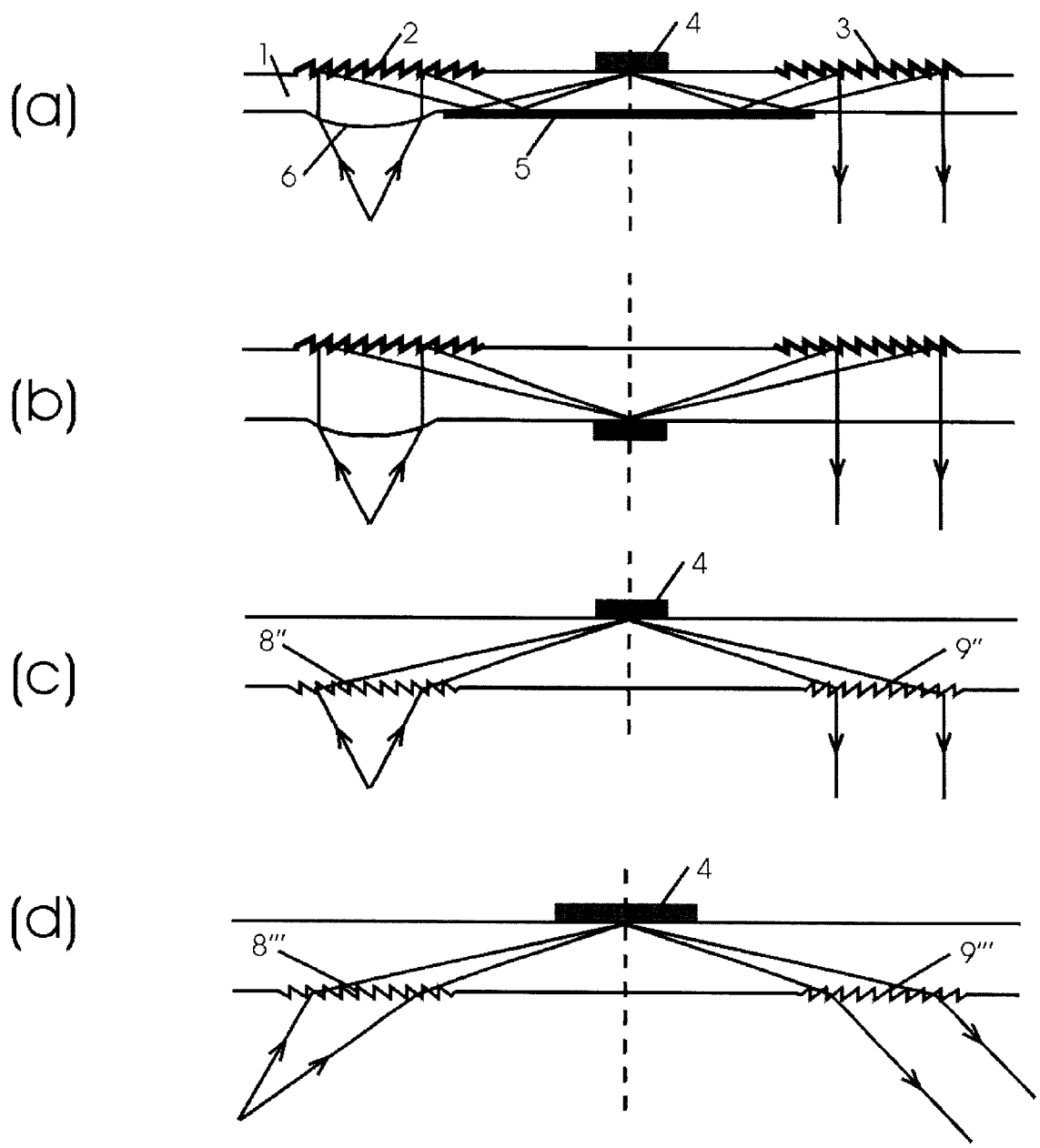

FIG. 2 Schematics of cross-sectional views of 4 different configurations of diffraction gratings on SPR sensor chips as formed by the method of the present invention. The input light beams originate from point sources or line sources and the output light beams are collimated.

Figure 3:
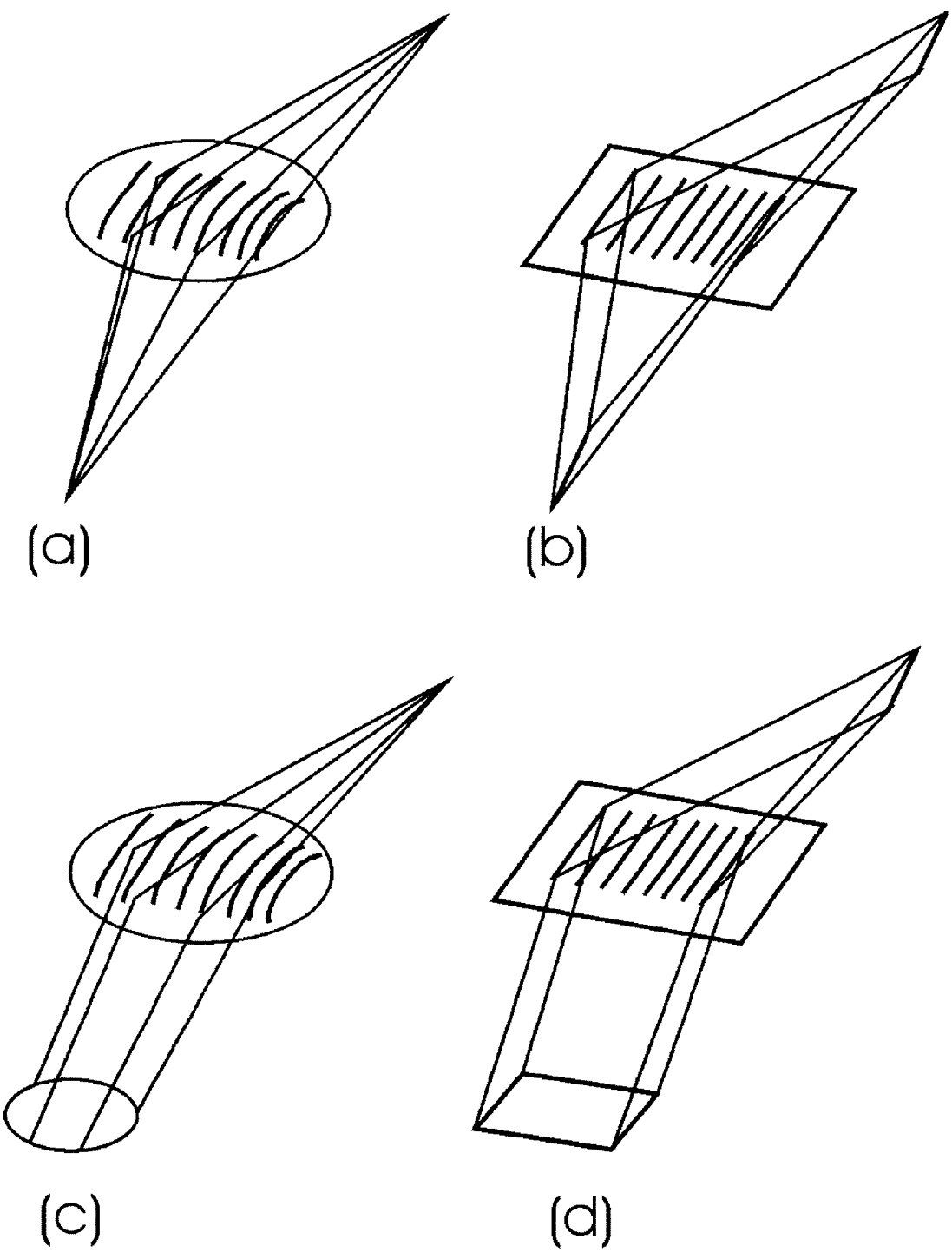

FIG. 3 Schematics of the imaging functions of the transmission diffraction gratings integrated on the SPR sensor chips with 4 examples of functions: (a) a point light source is imaged to a point, (b) a line light source is imaged onto a line, (c) a collimated light source is imaged to a point and (d) a collimated light source is imaged to a line.

Figure 4:
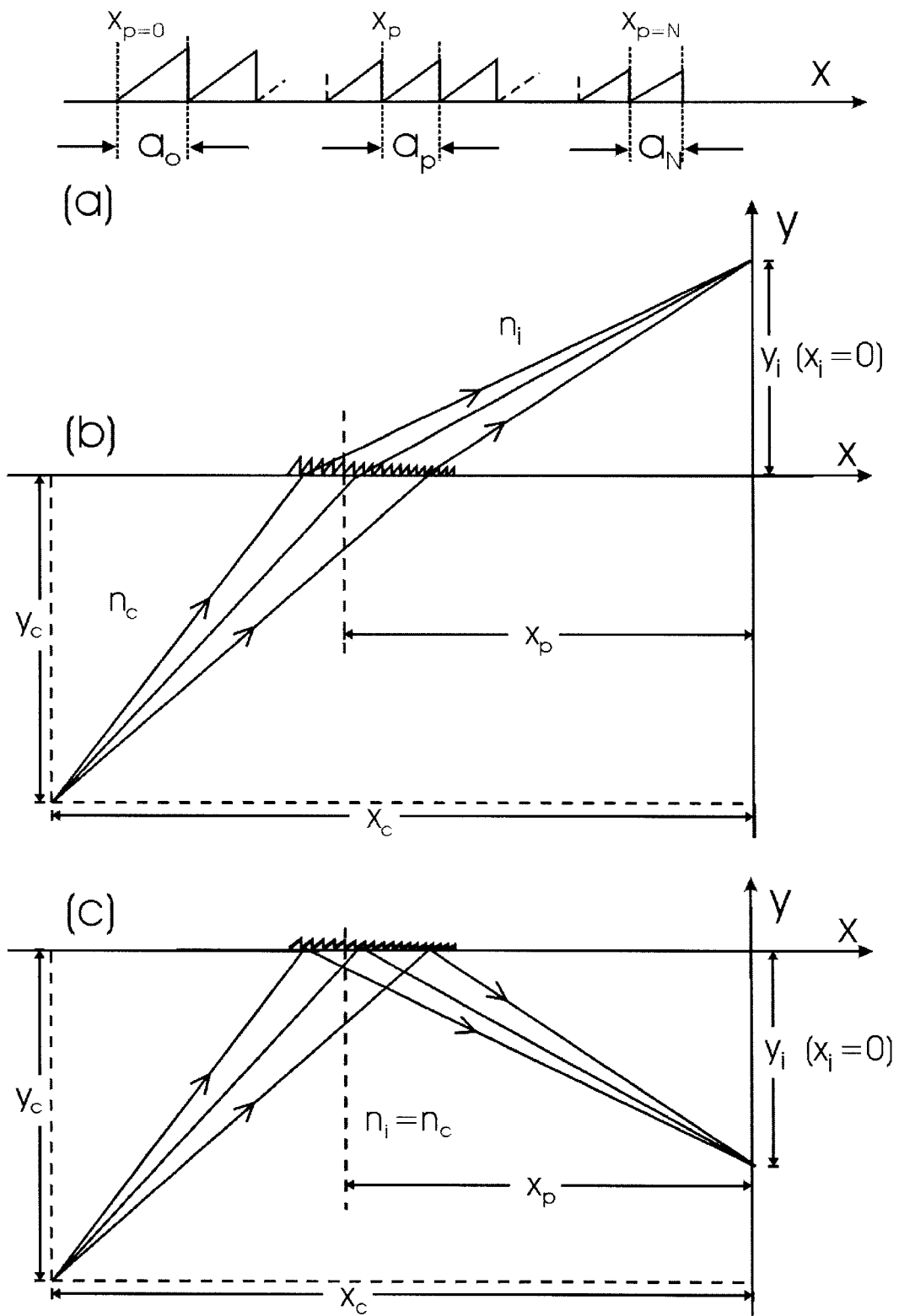
Figure 4:
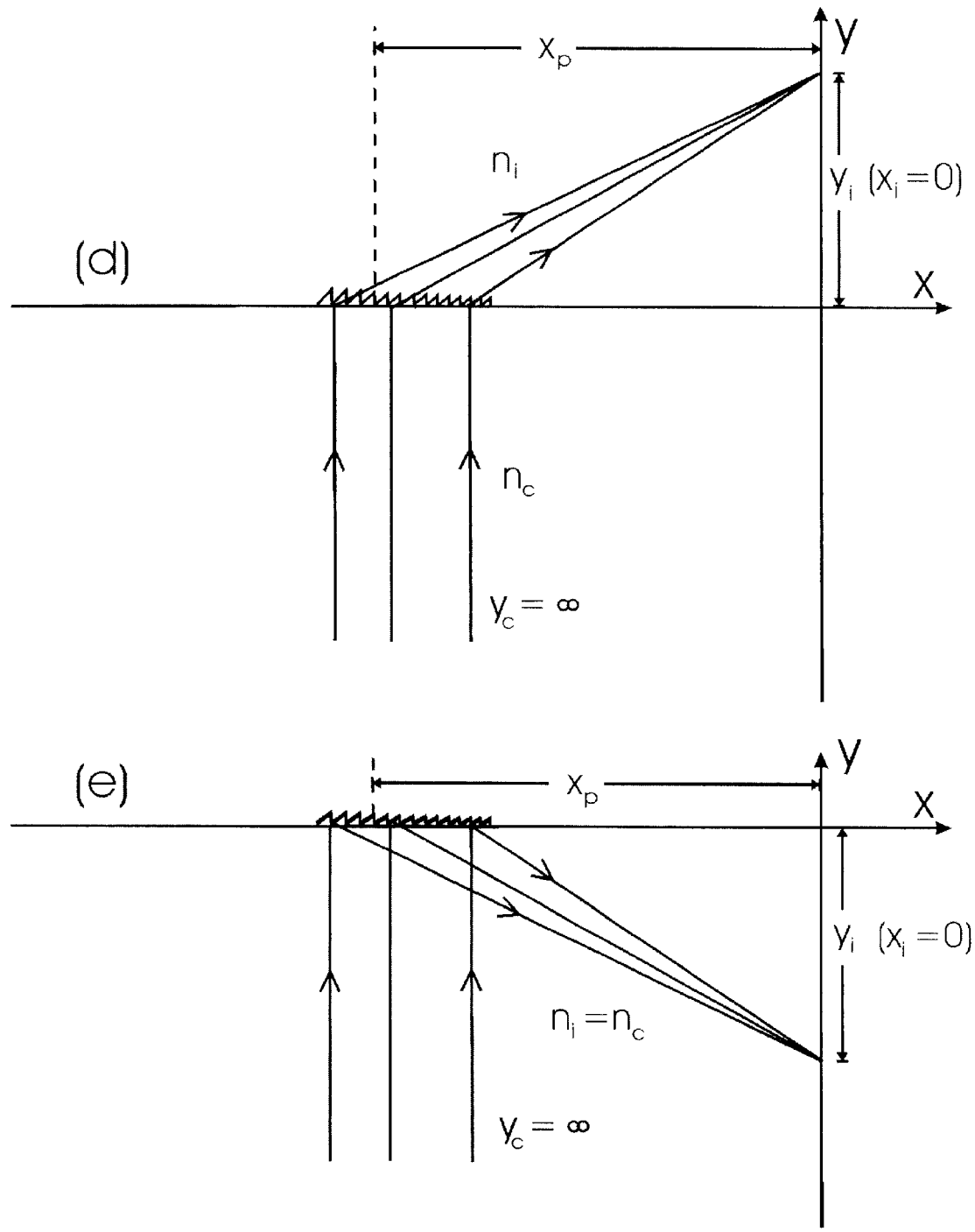

FIG. 4 Schematics of cross-sectional views of diffraction grating structures with (a) definition of the grating elements, (b) a transmission diffraction grating imaging a reconstruction point (line) in an external medium onto an image point (line) in the body of the SPR sensor chip, (c) a reflection diffraction grating imaging a reconstruction point (line) onto an image point (line) inside the body of the SPR sensor chip, (d) a transmission diffraction grating imaging a collimated ray in an external medium onto an image point (line) in the body of the SPR sensor chip, and (e) a reflection diffraction grating imaging a collimated ray onto an image point (line) inside the body of the SPR sensor chip.

Figure 5:
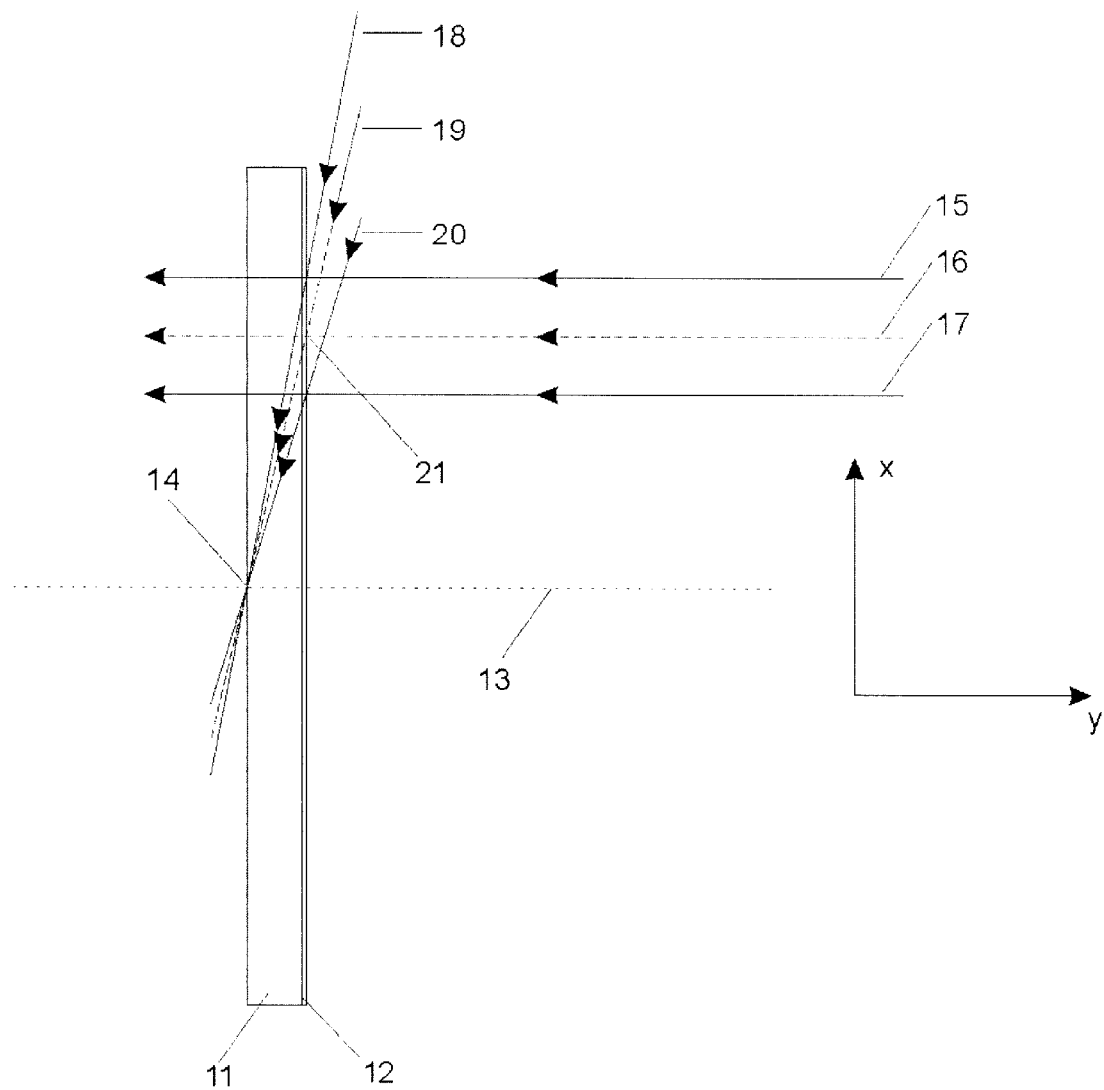

FIG. 5 Schematics of the oblique angle holographic method of formation of the first transmission diffraction grating (8) in FIG. 1(c). The recording wavelength is assumed to be identical to the effective reconstruction wavelength.

Figure 6:
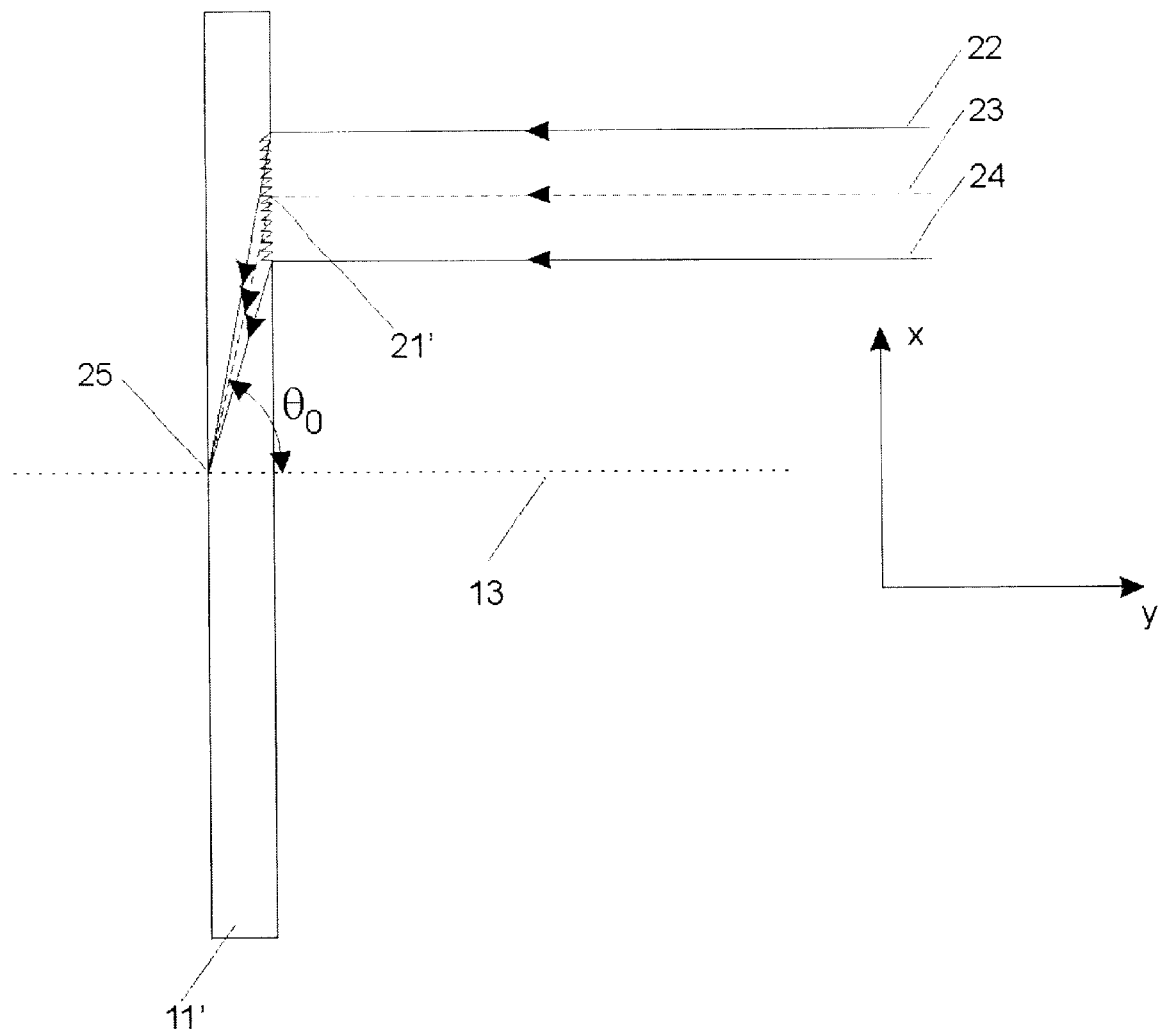

FIG. 6 Schematics of the function of the transmission diffraction grating as formed with the method illustrated in FIG. 5.

Figure 7:
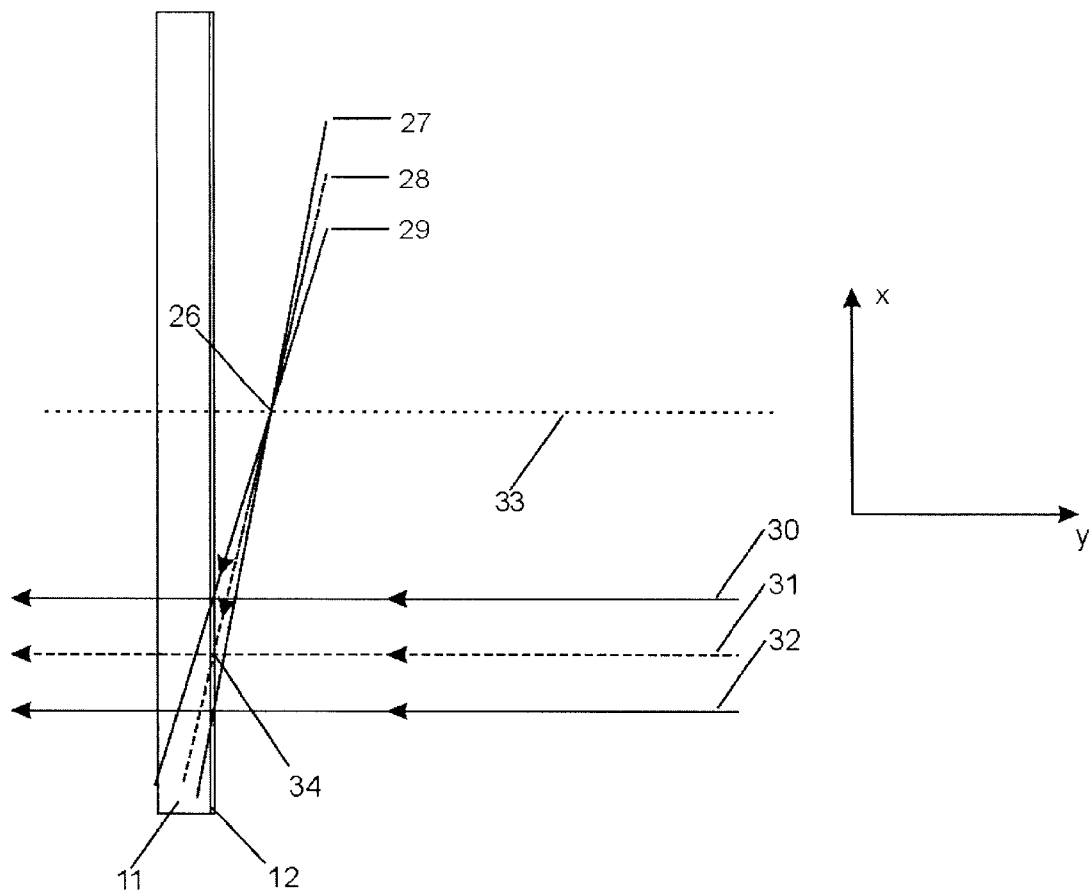

FIG. 7 Schematics of the oblique angle holographic method of formation of the first reflection diffraction grating (2) in FIG. 1(b). The recording wavelength is assumed to be identical to the effective reconstruction wavelength.

Figure 8:
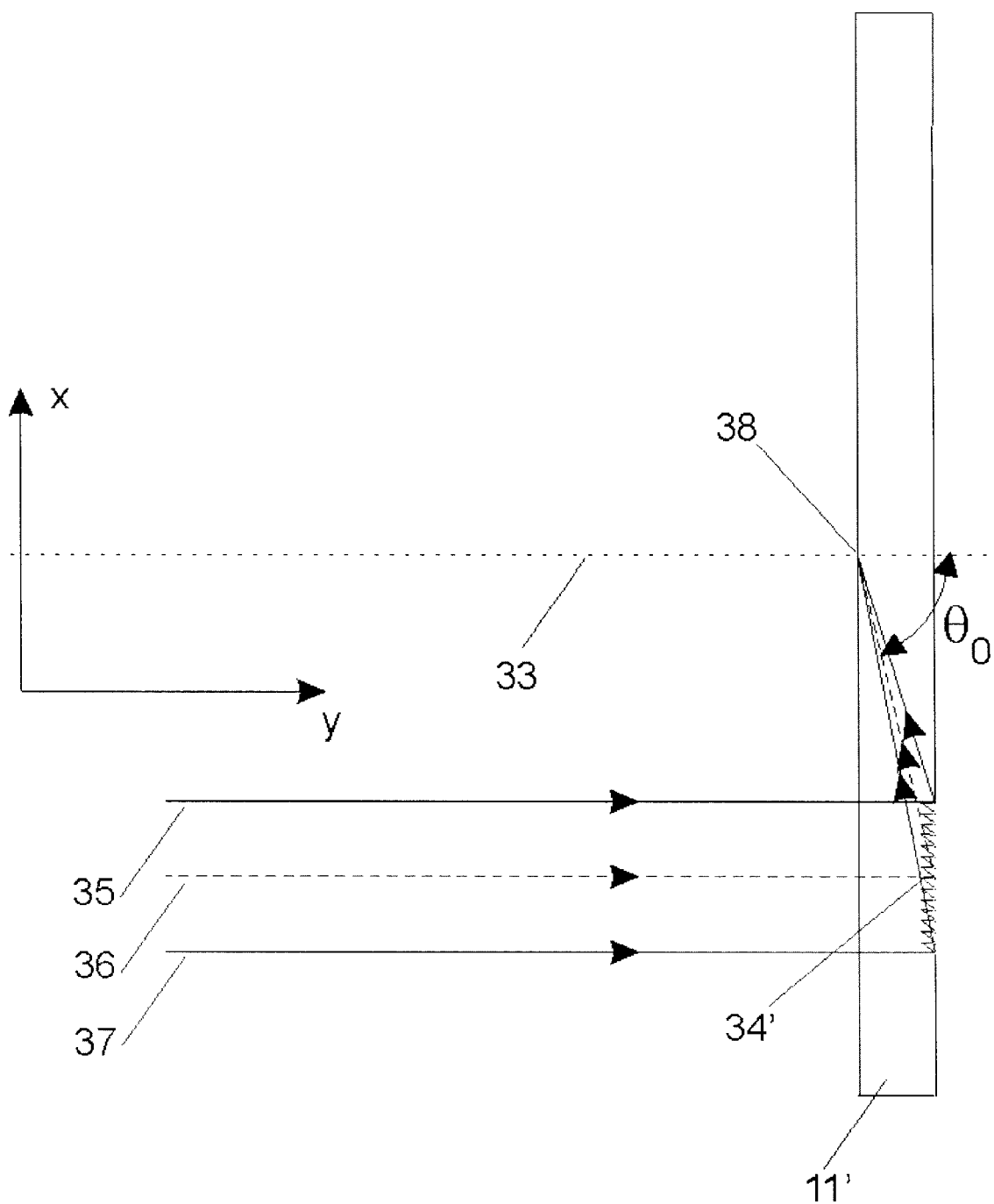

FIG. 8 Schematics of the function of the reflection diffraction grating as formed with the method illustrated in FIG. 7.

Figure 9:
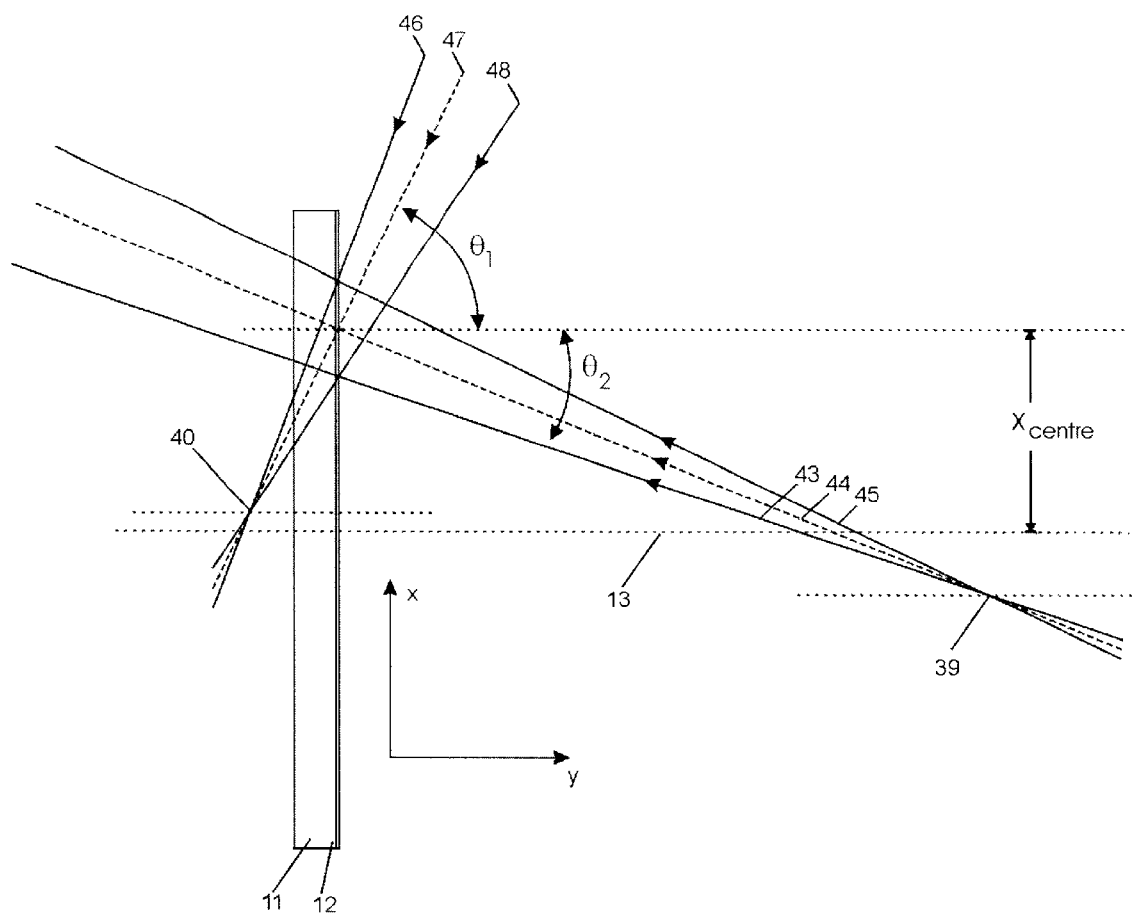

FIG. 9 Schematics of the oblique angle holographic method of formation of the first transmission diffraction grating (8) in FIG. 1(c). The recording wavelength and the effective reconstruction wavelength are different, and compared to FIG. 5 compensations in the positions and angular energy distributions have to be made for the recording waves.

Figure 10:
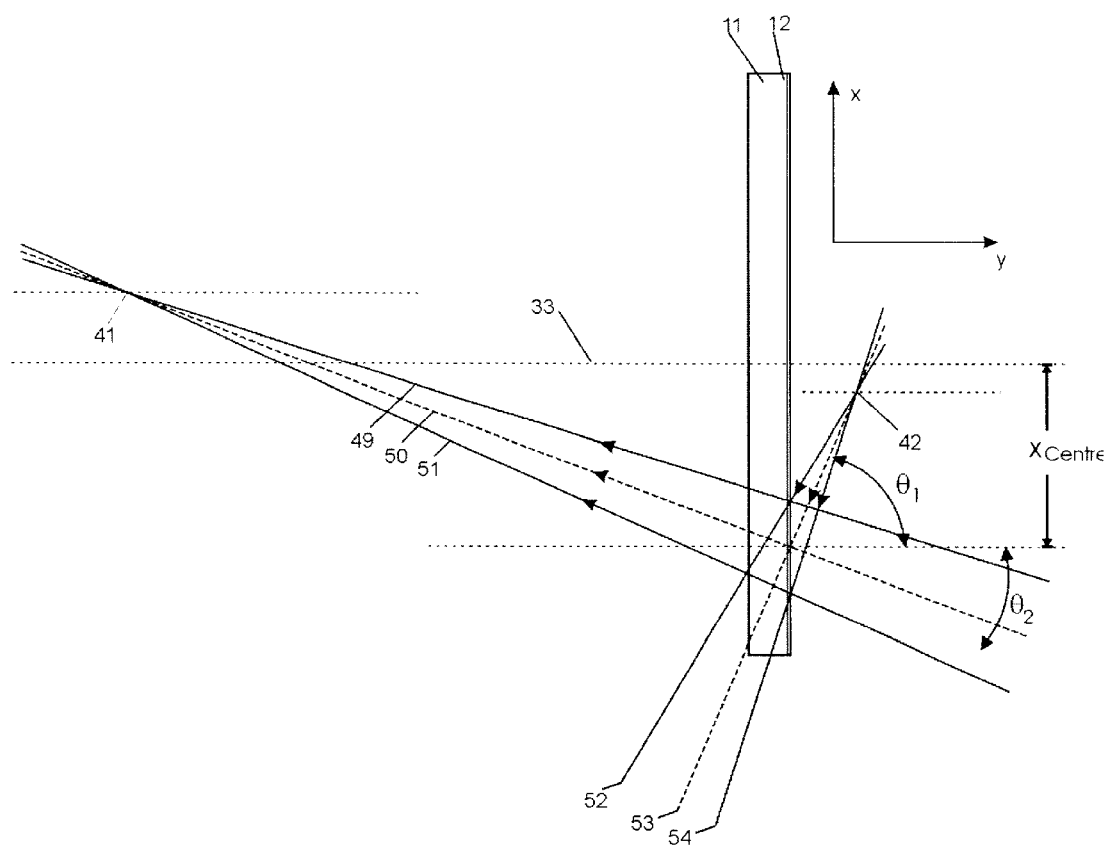

FIG. 10 Schematics of the oblique angle holographic method of formation of the first reflection diffraction grating (2) in FIG. 1(b). The recording wavelength and the reconstruction wavelengths are different, and compared to FIG. 7 compensations in the positions and angular energy distributions have to be made for the recording waves.

Figure 11:
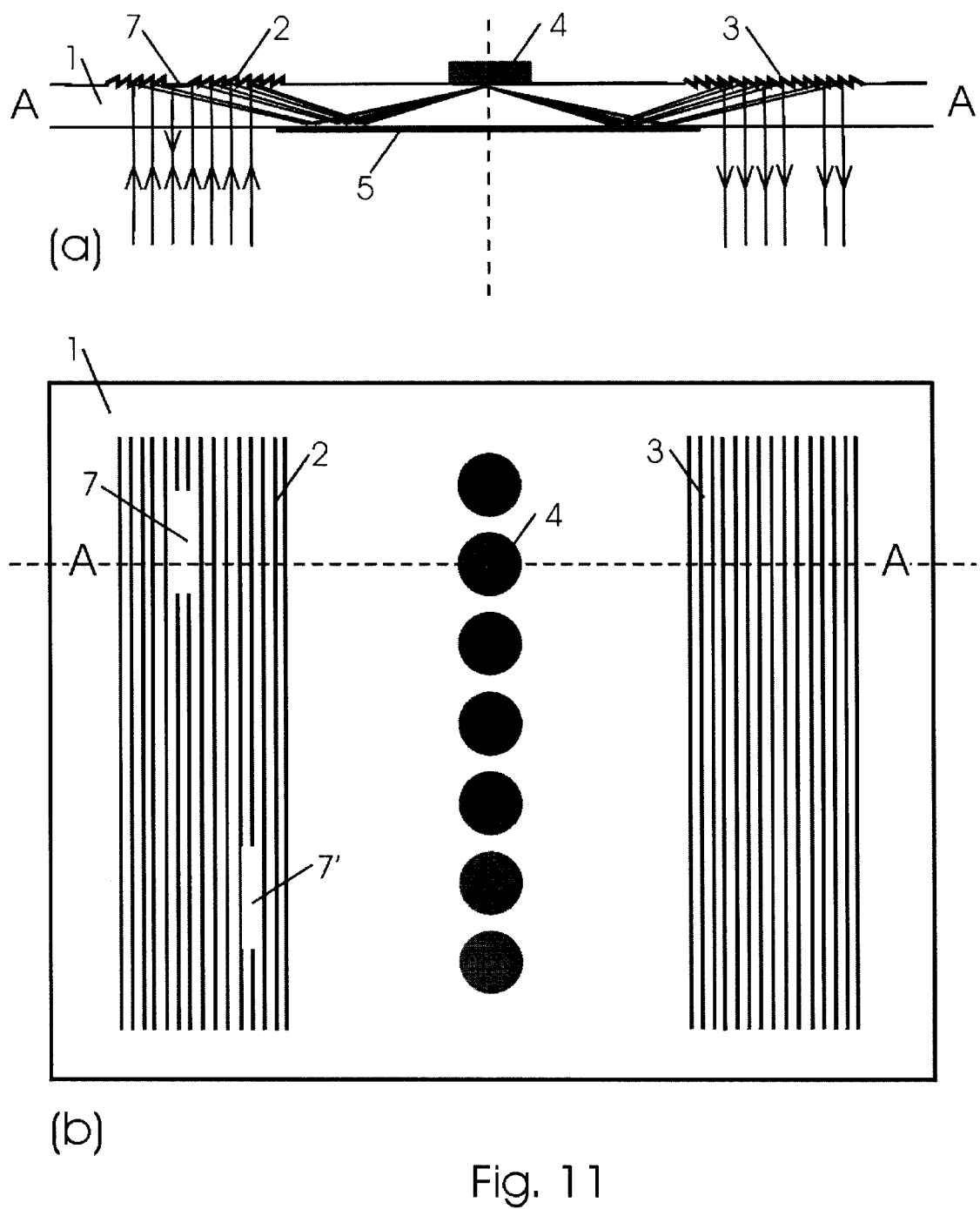

FIG. 11 Schematics of an SPR sensor chip with calibration marks (7) and (7') for the input light beam as formed by the method of the present invention, where (a) is a cross-sectional view along A—A and (b) is a top view of the SPR sensor chip.

FIG. 1 illustrates cross-sectional views of 5 different configurations of diffraction gratings on SPR sensor chips as formed by the method of the present invention.

In FIG. 1(a), the SPR sensor chip comprises a body of a transparent material (1), a first reflection diffraction grating (2), a second reflection diffraction grating (3), a sensing domain (4) comprising an SPR metal film with a superstrate of a sensing area on the top, and a mirror (5) on the backside surface of the SPR sensor chip. The input to the SPR sensor chip is essentially a collimated light beam, and the output light beam is essentially also a collimated light beam. The light sources can be monochromatic light sources like semiconductor lasers, narrow band light sources like light emitting diodes. In order to reduce dispersion effects caused by broad wavelength band light incident onto the diffraction grating, light emitting diodes with broad band emissions can be combined with a narrow bandwidth filter. The detectors can be photodiodes, photodiode arrays, charge-coupled-devices, complementary metal oxide semiconductor image sensors or the like. The mirror (5) can be a metal like gold, silver, aluminium or the like, or the bare interface between the backside surface of the SPR sensor chip substrate and the surrounding medium, which is usually air.

The function of the SPR sensor chip in FIG. 1(a) is the following. The first diffraction grating (2) focuses the input light beam via the mirror (5) onto the sensing domain (4) and the second diffraction grating transforms the light beam into an output collimated light beam. FIG. 1(b) is an alternative configuration without the mirror and where the sensing domain is positioned at the same side as the input light beam and output light beam.

FIG. 1(c) is a configuration with transmission diffraction gratings. The SPR sensor chip comprises a body of a transparent material (1), a first transmission diffraction grating (8), a second transmission diffraction grating (9), and a sensing domain (4). The input to the SPR sensor chip is essentially a collimated light beam, and the output light beam is essentially also a collimated light beam. The first transmission diffraction grating (8) focuses the input light beam onto essentially a point or a line under the sensing domain (4).

FIG. 1(d) illustrates an alternative configuration, where the input light beam with an angle ($\theta_{in}$) is incident to the diffraction grating (8') and the output light beam with an angle ($\theta_{out}$) is exiting the diffraction grating (9'). The angle $\theta_{in}$ in FIG. 1(d) is defined to be positive, if the extrapolated ray incident on the diffraction grating (8') intersects the symmetry plane or symmetry axis (10) above the sensor chip. If this ray intersects (10) below the sensor chip, the angle $\theta_{in}$ is defined to be negative. The angle $\theta_{out}$ in FIG. 1(d) is defined to be positive, if the extrapolated ray diffracted from the diffraction grating (9') intersects the symmetry plane or symmetry axis (10) above the sensor chip. If this ray intersects (10) below the sensor chip, the angle $\theta_{in}$ is defined to be negative. The drawing in FIG. 1(d) illustrates the case, where both $\theta_{in}$ and $\theta_{out}$ are positive.

For the gratings in FIG. 1, there are two first order diffracted waves, +1 and −1; but only the dominant first order diffracted waves are illustrated. Optimum diffraction efficiency of the gratings (8') and (9') on the SPR sensor chip in FIG. 1(d) is achieved, when $\theta_{in}$ and $\theta_{out}$ are both sufficiently negative to yield an evanescent wave for one of the first order diffracted waves. Most of the diffracted light energy then occurs in the other first order diffracted wave and a diffraction efficiency close to 100% can be achieved. Typically, for the diffraction grating structures in FIGS. 1(a–c) with perpendicularly incident light, the diffraction efficiency is considerably lower (up to ~40%). The advantages of higher diffraction efficiencies with the configuration of negative $\theta_{in}$ and $\theta_{out}$ in FIG. 1(d) compared to the configurations in FIGS. 1(a–c) are obtained with penalties in more complicated mounting of the light source (LS) and the light detector (LD), and more critical alignment of the sensor chip relative to the LS and LD. For SPR sensors, the light power available from the LS is usually sufficient and the grating efficiency does not need to be fully optimised.

FIG. 1(e) shows a configuration where the input light beam is collimated, but the grating (3') is made in such a manner that the output beam is slightly diverging from the sensor chip. The purpose is to optimise the sensitivity of the SPR sensor chip, and the divergence angle is chosen in order to match the output beam size with the size of the detector array. Due to refraction effects, the divergence angle $\theta_{div}$ must not be excessively large preventing the sensor chip from working sufficiently well. In other configurations, the sensitivity is more readily optimised by having a finite convergence angle in order to match the output beam size with the size of the detector array. Other configurations cover sensor chips, where the output grating is a transmission grating with a finite divergence angle or a finite convergence angle. The magnitude of the convergence angles or divergence angles are in the range from 0° to 20°.

FIG. 2 illustrates cross-sectional views of 4 additional configurations of diffraction gratings on SPR sensor chips as formed by the method of the present invention. In the configurations in FIGS. 2(a)–(d), the input light beam is not collimated, but originates from either a point source or a line source. In FIG. 2(a), the SPR sensor chip comprises a body of a transparent material (1), a first reflection diffraction grating (2), a second reflection diffraction grating (3), a sensing domain (4), a mirror (5), an integrated lens acting as a collimator (6). The function of the SPR sensor chip in FIG. 2(a) is the following. The input light beam being a point source or a line source is collimated via the integrated lens (6), the first diffraction grating (2) focuses the light beam onto the sensing domain and the second diffraction grating collimates it and transforms it to an output light beam. FIG. 2(b) is an alternative configuration without the mirror and where the sensing domain (4) is positioned at the same side as the input and output light beams.

FIG. 2(c) is a configuration with transmission diffraction gratings. The SPR sensor chip comprises a body of a transparent material (1), a first transmission diffraction grating (8''), a second transmission diffraction grating (9''), and a sensing domain (4). The input to the SPR sensor chip is essentially a point source or a line source and the first reflection diffraction grating (8'') may focus the input light beam onto essentially a point or a line under the sensing domain (4) and the second diffraction grating (9'') transforms the light beam into an output light beam exiting the SPR sensor chip. In FIG. 2(c), the centre of the input light beam and the centre of the output light beam are perpendicular to the diffraction gratings (8'') and (9''), respectively. FIG. 2(d) illustrates an alternative configuration, where the centre of the input light beam and centre of the output light beam exhibit an angle different from zero to the diffraction gratings (8''') and (9'''), respectively.

FIG. 3 illustrates the imaging function of the transmission diffraction gratings integrated on the SPR sensor chips with 4 examples of functions: (a) a point light source is imaged to a point, (b) a line light source is imaged onto a line, (c) a collimated light source is imaged to a point and (d) a collimated light source is imaged to a line. The present invention covers other configurations of transmission diffraction gratings where a pre-known angular energy distribution of an input light beam can be imaged onto a surface of the SPR sensor chip in a point, an array of points, a spot, an array of sports, a line, an array of fractions of lines, a curve, or an array of fractions of curves. Reflection diffraction gratings have similar functions.

FIG. 4 shows cross-sectional views of diffraction grating structures according to the present invention. In FIG. 4(a), the definition of the grating elements is illustrated, where $a_0$ is the first grating element positioned at $x_{p=0}$, $a_p$ is the p'th grating element positioned at $x_p$ and $a_N$ is the last grating element of the diffraction grating positioned at $x_{p=N}$.

FIG. 4(b) illustrates a cross-sectional view of a transmission diffraction grating from FIGS. 3(a) and (b). A reconstruction point ($x_c$, $y_c$) in the external medium with the refractive index $n_c$ (typically air) is imaged onto an image point ($x_i$, $y_i$) in the body of the SPR sensor chip with the refractive index $n_i$. FIG. 4(c) illustrates a cross-sectional view of the corresponding reflection diffraction gratings. A reconstruction point ($x_c$, $y_c$) in the body of the SPR sensor chip with the refractive index $n_i$ is imaged onto an image point ($x_i$, $y_i$) in the body of the SPR sensor chip.

Assuming that the image point, the reconstruction point and the grating element are positioned in the same x-y plane as defined in FIG. 4, the grating spacing for either the transmission diffraction grating in FIG. 4(b) or the reflection diffraction rating in FIG. 4(c) is determined by the expression, $$a_p = \frac{m\lambda}{n_g} \left[ \frac{x_p}{\sqrt{x_p^2 + y_i^2}} - \frac{x_c - x_p}{\sqrt{(x_c - x_p)^2 + y_c^2}} \right]^{-1}, \quad (2)$$

where all quantities are positive. Eqn. (2) is on a scalar form, but it can readily be modified to a vector form taking into account the case where the image point, the reconstruction point and the grating element are not positioned in the same x-y plane.

FIG. 4(d) illustrates a cross-sectional view of the transmission diffraction gratings from FIGS. 3(c) and (d). A collimated reconstruction light beam in an external medium with the refractive index $n_c$ (typically air) is imaged onto an image point $(x_i, y_i)$ in the body of the SPR sensor chip with the refractive index $n_i$. FIG. 4(e) illustrates a cross-sectional view of the corresponding reflection diffraction gratings. A collimated light beam in the body of the SPR sensor chip with the refractive index $n_i$ is imaged onto an image point $(x_i, y_i)$ in the body of the SPR sensor chip. The expression of the grating periodicity for the gratings illustrated in FIGS. 4(d) and (e) is given by eqn. (1). It can be derived from eqn. (2) setting $y_c \rightarrow \infty$ or $x_c \rightarrow x_p$.

In order to characterise the diffraction grating, eqns. (1) and (2) can be written in terms of the dimensionless parameter $(a_p n_g / m\lambda)$. Eqn. (1) now reads;

$$\frac{a_p n_g}{m\lambda} = \left(\frac{y_i}{x_p}\right)\left[1 + \left(\frac{x_p}{y_i}\right)^2\right]^{1/2}, \quad (3)$$

and eqn. (2) now reads;

$$\frac{a_p n_g}{m\lambda} = \left[\frac{\left(\frac{x_p}{y_i}\right)}{\sqrt{\left(\frac{x_p}{y_i}\right)^2 + 1}} - \frac{\left(\frac{x_c}{y_i}\right) - \left(\frac{x_p}{y_i}\right)}{\sqrt{\left(\frac{x_c - x_p}{y_i}\right)^2 + \left(\frac{y_c}{y_i}\right)^2}}\right]^{-1}, \quad (4)$$

where the diffraction grating parameters $(x_p/t)$, $(x_c/t)$ and $(y_c/t)$ [see FIG. 4] have been normalised with respect to $y_i$. For an SPR sensor chip, the SPR angle is in the angular range from 40° to 80° implying that $0.8 < (x_p/y_i) < 6$. Assuming a collimated input light beam, according to eqn. (3) the corresponding change in the dimensionless parameter $a_p n_g / m\lambda$ is from 1.6 to 1.0. Assuming that the input light beam to the diffraction grating rather originates from a point/line source positioned underneath the centre of the diffraction grating with a centre angle coupling to the sensing domain of 73° corresponding to $x_c/t = 3.4$ and with a typical angular spatial distribution of 35°, the parameter $(y_c/t)$ is then 3.7 and eqn.(4) yields a variation in the dimensionless parameter from 20 to 0.6.

The oblique angle holographic method of formation of the first transmission diffraction grating in FIG. 1(c) is illustrated in FIG. 5 for the case where the recording wavelength is identical to the reconstruction effective wavelength (i.e. the wavelength of the light illuminating the SPR layer). In FIG. 6, the function of the transmission diffraction grating is illustrated. FIGS. 5–6 relate to the diffraction grating configurations in FIGS. 3(c)–(d), but the present method is not limited to these cases. A master substrate of glass or the like (11) is spin coated on a plane first surface with a photosensitive film (12) like a negative photoresist film with a thickness of 0.5–3 μm. The photosensitive film is pre-exposed with a UV lamp, typically in a few seconds, in order to achieve a linear regime in the holographic recording process afterwards.

The photosensitive film is simultaneously illuminated by two overlapping light waves originating from the same monochromatic and coherent light source emitting a wavelength where the polymeric photosensitive film is sensitive to structural changes in the polymer. The monochromatic and coherent light source is preferably a gas laser such as a HeCd laser, a Kr laser, or an excimer laser; but a semiconductor diode laser of sufficient quality may also be used. One light wave referred to as the object wave is a light wave that under an oblique angle is focussed to a desirable focal point (14) and consisting of light rays in the angular range from ray (18) to ray (20) in FIG. 5. Because of refraction effects of the light rays (18) to (20) hitting the master substrate (11), the position of the focal point may be changed by the presence of the master substrate. The point (14) is therefore obtained as the point positioned at the intersection between the rays (18) to (20) extended into the master substrate (11). The point (14) would be identical to the focus point of the rays (18) to (20) provided that the refractive indices of the master substrate, the photosensitive film and the surrounding medium were identical.

A second light wave referred to as the reference wave with rays (15)-(17) in FIG. 5 is collimated and incident in the same direction as the desirable direction of the reconstruction wave, i.e. the input collimated light beam to the SPR sensor chip. The photosensitive film is exposed by the overlapping object waves and reference waves to form an interference pattern (21) with a suitable exposure time in order to ensure the right depth of the diffraction gratings and optimise the diffraction efficiency. The exposure time is adjusted in order to ensure the right grating depth of the diffraction grating. For a typical photosensitive film like the negative photoresist Shipley S1828 exposed to a total light intensity ~5 W/m² at a wavelength of 442 nm of the object wave and the reference wave, the exposure time is 30–50 sec. The photosensitive film is subsequently developed to create the surface relief pattern that is transferred to form the transmission diffraction grating (21') on a replicated substrate (11') as illustrated in FIG. 6. The transmission diffraction grating has the desirable property of directing and focussing a collimated reconstruction light beam with rays (22)-(24) incident on (21') to a focal point (25) in FIG. 6 essentially with a position from the centre of the diffraction grating (21') identical to the position of the point (14) relative to the centre of the interference pattern (21) in FIG. 5.

The object wave illuminates the plane of the photosensitive film under an oblique angle of incidence, typically with an angular range of 10°–20° and with a central angle of incidence ($\theta_c$) being close to the SPR angle of the SPR sensor chip and lying in the range 40°–80°. The oblique angle of incidence causes the light intensity of the object wave to vary considerably across the exposed area on the photosensitive film. This is due to various effects including the variation in the distance from the focal point of the object wave to the plane of the photosensitive film, the angular distribution of the object wave incident on the photosensitive film and the angular dependence of the reflection from the photosensitive film. It is possible to make corrections for these variations in light intensity during exposure by changing the angular light energy distribution of the object wave, the reference wave or both. This can for example be performed by applying a variable density beamsplitter when splitting the object wave and the reference wave originating from the same light source or applying variable density filters or mirrors to the object wave, the reference wave or both. An alternative method is to make use of the intensity distribution of the Gaussian profile of the object wave, the reference wave or both.

The oblique angle holographic method according to the present invention can be extended to form a second transmission diffraction grating as (9) in FIG. 1(c). After the process step of light exposing the first transmission diffraction grating, the substrate (11) is rotated 180° around an axis (13) intersecting the point (14) and being normal to the plane first surface of the master substrate covered by the spin-coated photosensitive film (12). The second diffraction grating is exposed with the same conditions as the first diffraction grating and it will therefore appear as the mirror image of the first diffraction grating as illustrated in FIG. 1(c). The alignment can readily be made, since it is only a matter of aligning the point (14) to the axis (13) and rotating the substrate.

The transmission diffraction gratings (8") and (9") in FIG. 2(c) and the transmission diffraction gratings (8'") and (9'") in FIG. 2(d) can be made in a similar way. The difference is that in the case of recording the diffraction gratings (8") and (8'"), the aforesaid second light wave referred to as the reference wave with rays (15)-(17) in FIG. 5 now originates from a point positioned at the same position and with the same angular energy distribution as the desired source of the input reconstruction light rays (i.e. rays from the light source as input to the SPR sensor chips) to the SPR sensor chip. The oblique angle holographic method of formation of diffraction gratings in SPR sensor chips can be extended to include reconstruction light sources with more involved angular energy distributions and SPR sensor chips comprising other image patterns on the sensing domain. The object wave exhibits a pattern on a plane parallel to the plane first surface of the master substrate, which is identical to the desirable pattern on the SPR sensor chip, and the angular energy distribution of the reference wave is identical to the angular energy distribution of the reconstruction wave. The first diffraction grating of the SPR sensor chip will image the light source onto the desirable pattern on the sensing domain and the second diffraction grating will return the light at the output of the SPR sensor chip with an angular energy distribution similar to the input. Alternatively, the second diffraction grating may be recorded with the same object wave as the first diffraction grating, but with a different angular distribution of the reference wave in order to optimise the coupling to the optical detector collecting the light from the output of the SPR sensor chip.

The oblique angle holographic method according to the present invention of formation of the first reflection diffraction grating (2) in FIG. 1(b) and FIG. 2(b) is illustrated in FIG. 7 for the case where the recording wavelength and the reconstruction input light beam to the SPR sensor chip are identical. The function of the reflection diffraction grating is illustrated in FIG. 8. A plane master substrate of glass or the like (11) is spin coated with a photosensitive film (12) with a thickness of 0.5-3 µm and a pre-exposure process as described above. The photosensitive film is simultaneously illuminated by two overlapping light waves originating from the same monochromatic and coherent light source forming an interference pattern (34). One light wave referred to as the object wave is a light wave that under an oblique angle is focussed to a desirable point (26) and consisting of light rays in the angular range from ray (27) to ray (29) in FIG. 7. The point (26) is positioned at the focal point of the rays (27) to (29) and at a distance from the plane first surface of the master substrate equal to the thickness of the replicated substrate (11').

A second light wave referred to as the reference wave with rays (30)–(32) in FIG. 7 is collimated and incident in the same direction as the desired direction of the reconstruction input collimated light rays to the SPR sensor chip. The photosensitive film is exposed by the overlapping object waves and reference waves in a suitable exposure time in order to ensure the right depth of the diffraction gratings and optimise the diffraction efficiency. The photosensitive film is subsequently developed to create the surface relief pattern that is transferred to form the reflection diffraction grating (34') on a replicated substrate (11') as illustrated in FIG. 8. The reflection diffraction grating (34') has the desirable property of directing and focussing a collimated light beam with rays (35)–(37) incident on (34') to a focal point (38) in FIG. 8 essentially with a position from the centre of the diffraction grating (34') identical to the position of the reflection point of (26) in FIG. 7 with respect to the plane first surface of the substrate (11) relative to the centre of the interference pattern (34).

The oblique angle holographic method can be extended to form a second reflection diffraction grating as (3) in FIG. 1(b) and FIG. 2(b). After the process step of light exposing the first reflection diffraction grating, the master substrate (11) is rotated 180° around an axis (33) intersecting the point (26) and being normal to the plane first surface of the master substrate (11). The second reflection diffraction grating is exposed with the same conditions as the first reflection diffraction grating and it will therefore appear as the mirror image of the first reflection diffraction grating. The reflection diffraction gratings in FIG. 1(a) and FIG. 2(a) can be made in the same way as in FIG. 1(b) and FIG. 2(b), the only difference being that the thickness of the sensor chips in FIG 1(a) and FIG. 2(a) is half of the thickness of the sensor chips in FIG. 1(b) and FIG. 2(b), respectively.

In most practical cases, the effective wavelengths of the recording light waves and the reconstruction light waves to the SPR sensor chip are different, which is either due to different wavelengths of the recording light sources and the reconstruction light sources and/or differences in the refractive indices of the replicated substrate (11') and the surrounding medium. In order to minimise optical aberrations in these situations, one has to compensate for the change in the effective wavelengths (i.e. the wavelength divided by refractive index) by modifying the recording setup. In general, the object wave and the reference wave both have to be focusing or defocusing waves and their focal points will be positioned off the central axis (13) in FIG. 5 and (33) in FIG. 7. The modified recording setups, which lead to minimum optical aberrations for the transmission and reflection gratings shown in FIGS. 6 and 8, one from the object wave and one from the reference wave, are illustrated schematically in FIGS. 9 and 10, respectively.

The method according to one aspect of the present invention to make such corrections is the following. If two light rays illuminating a photosensitive film form a light interference pattern, the grating spacing $a_{record}$ between two lines of the interference pattern for the diffraction grating is given by;

$$a_{record} = \frac{\lambda_{record}}{\sin(\theta_1) + \sin(\theta_2)}, \quad (5)$$

where $\lambda_{record}$ is the recording wavelength and $\theta_1$ and $\theta_2$ are the angles of incidence of the two rays (see FIGS. 9 and 10).

For a collimated reconstruction wave at normal incidence being diffracted in the replicated substrate (11') at an angle $\theta_0$ (see FIGS. 6 and 8), the grating spacing for the diffraction grating $a_{read}$ is given by $$a_{read} = \frac{\lambda_{read}}{n_g \sin(\theta_0)}, \quad (6)$$

where $\lambda_{read}$ is the reconstruction vacuum wavelength and $n_g$ is the refractive index of the replicated substrate (11'). In order to obtain minimum aberrations, the procedure is to use the two expressions (5) and (6) and vary the focal positions of the object wave and reference wave until the difference between $a_{record}$ and $a_{read}$ is minimum. This is achieved by expanding to third order the expression $a_{record}$-$a_{read}$ as a function of the direction perpendicular to the lines of the interference pattern (x):

$$\alpha_{record}(x)-\alpha_{read}(x)=A_0+A_1(x-x_{centre})+A_2(x-x_{centre})^2+A_3(x-x_{centre})^3, \quad (7)$$

where $x_{centre}$ is the centre position of the interference pattern. The coefficients $A_0$, $A_1$, $A_2$, and $A_3$ depend on the positions of the reference focus $\{x_r, y_r\}$ being (39) and (41) in FIGS. 9 and 10, respectively, and the object focus $\{x_0, y_0\}$ being (40) and (42) in FIGS. 9 and 10, respectively. In order to minimise aberrations, the following four sets of equations must be solved:

$$A_0(x_r, y_r, x_0, y_0)=0$$

$$A_1(x_r, y_r, x_0, y_0)=0$$

$$A_2(x_r, y_r, x_0, y_0)=0$$

$$A_3(x_r, y_r, x_0, y_0)=0$$

The four equations are non-linear, and they have to be solved using numerical methods. A good guess to the real solution is needed as a starting point. Here, the analytical set of approximate solutions derived in J. Latta, Appl. Opt. 10, 599 (1971) is a good choice.

The formula in eqn.(6) is for the case of a collimated reconstruction wave at normal incidence. However, the method of the present invention also covers cases of a non-collimated reconstruction wave with an angle of incidence ($\theta_i$) different from zero (see the configurations in FIG. 1(d) and FIGS. 2(c–d)). Eqn. (6) is then modified according to;

$$a_{read} = \frac{\lambda_{read}}{n_g(\sin(\theta_0) - \sin(\theta_i))}. \quad (6')$$

FIGS. 9 and 10 are schematic illustrations of positions of the object wave and the reference wave for transmission gratings and reflection gratings, respectively. In FIG. 9, the object wave comprising light rays in the angular range from ray (46) to ray (48) is focussed under an oblique angle to a desirable point (40) off the axis (13) intersecting the focal point (25) as defined in FIG. 6. The reference wave comprising light rays in the angular range from ray (43) to ray (45) is focussed to a desirable point (39) off the axis (13). In FIG. 10, the object wave comprising light rays in the angular range from ray (52) to ray (54) Is focussed under an oblique angle to a desirable point (42) off the axis (33) intersecting the focal point (38) as defined in FIG. 8. The reference wave comprising light rays in the angular range from ray (49) to ray (51) is focussed to a desirable point (41) off the axis (33).

The functions of the diffraction gratings in the SPR sensor chips can be further improved by fabricating calibration marks onto the surface relief structures. FIG. 11 illustrates an SPR sensor chip including calibration marks (7) and (7') on the input diffractive optical elements, where (a) is a cross-sectional view along A—A and (b) is a top view of the SPR sensor chip. Calibration marks are regions, where the grating structure has been removed. Light rays incident on such regions therefore do not diffract, but are simply reflected. This can be detected at the output of the sensor chip as a dark line or dark spot on the detector array. The calibration marks are made using the method of fabricating SPR sensor chips by overexposing the photosensitive film either before or after exposing the interference patterns for the diffraction gratings One purpose of these calibration marks is to calibrate the SPR sensor chip in terms of absolute values of the refractive index as measured by the SPR sensor, since the light rays incident onto the alignment marks correspond to an absolute value of an SPR angle and therefore an absolute value of the refractive index as measured by the SPR sensor. Another purpose of the calibration marks is to identify the orientation and position of the SPR sensor chip compared to the position of the detector array. A third purpose of the calibration marks is to correct for changes in the environment, e.g. wavelength shifts of the light source, mechanical vibrations or temperature drift causing the sensor chip to move. When such changes in the environment occur, the position of the calibration marks will move on the detector array, and the influence of environmental changes on the SPR response can be determined improving the sensitivity of the SPR sensor.

The calibration marks are preferably lines aligned parallel to the grating lines and there are preferably at least two calibration marks on one sensor chip, at least one being positioned at the high angle side (7) and at least one being positioned at the low angle side (7'). Alternatively, the calibration marks can be lines aligned perpendicularly to the grating lines. The width of the calibration marks is in the range 50–200 µm. The length of the calibration marks is in the range 0.5–5 mm. Calibration marks can also have other shapes than lines. They can be crosses, asterisks, circles, ellipses polygons, but the present invention is not limited to these shapes.

The key advantages with the oblique angle holographic method according to the present invention are the following. Firstly, the method according to the present invention creates the diffraction grating profile in one exposure step, which is fast, i.e. of the order of some seconds. This implies that thermal drift or other drift effects have a minimum effect. Secondly, the method according to the present invention requires no mechanical scanning that inherently increases the inaccuracies of the formation of the diffraction grating. The periodicity of the grating along the aperture is defined by the nature of the interference pattern created by the two recording laser beams. Thirdly, by positioning the two laser beams at the right positions, the method according to the present invention reduces aberrations to third order. Fourthly, diffraction gratings with various imaging functions including calibration marks can be generated applying the method according to the present invention and a pre-known angular energy distribution of the input light beam can be imaged onto a surface of the SPR sensor chip in the desirable pattern.

The master substrate with the formed surface relief pattern (SRP) can be used as an SPR sensor chip with the SRP acting as diffraction gratings. Alternatively, dry etching techniques like ion-milling, chemically assisted ion-beam etching or reactive ion etching can be used to sacrificial-layer etch the photosensitive film [K. Reimer et al., Proc. SPIE, 3226, Microelectronic Structures and MEMS for Optical Processing III, Austin, p.6 (1997)] in order to transfer the SRP into the master substrate. In the case of reflection diffraction gratings, the diffraction efficiency can be improved by disposing a metallic mirror on the top of the SRP. Metals are preferably gold, silver, aluminium or the like. The depth of the SRP can be adjusted by means of adjusting the exposure time and developing time of the photosensitive film in order to maximise the diffract ion efficiency for the metal selected to be disposed on the SRP. The metal is disposed either directly on the top of the developed photosensitive film by means of evaporation or sputtering or after performing a sacrificial-layer-etch.

A more preferable method of fabricating SPR sensor chips is the use of replication techniques such as hot embossing or moulding. An even more preferable method of fabricating SPR sensor chips is injection moulding or injection compression moulding, where a very large number of SPR sensor chips (several thousands) can be fabricated quickly, reproducibly and cheaply.

The process of transferring the master substrate with the desirable surface relief patterns (SRP) on the photosensitive film to diffraction gratings in injection/compression moulded SPR sensor chips is as follows. Using a sputtering technique, the master substrates are coated with a thin metal layer of a few hundred nanometers of a nickel/vanadium alloy or the like. As the next step, the substrates are emerged into a galvano-solution, where approximately 0.3 mm Ni is deposited on the substrate. The Ni plate is separated from the substrate now containing a negative image of the original SRPs. This Ni plate is referred to as the Ni shim or Ni master. The Ni shim is subsequently mounted into a suitable injection/compression moulding tool, where the shim is positioned in the mould cavity with the SRPs facing towards the cavity. When the SPR sensor chips are injection/compression moulded, the negative SRPs are transferred as a positive image to the moulded SPR sensor chip. The SRPs on the SPR sensor chip become true replicas of the original SRPs on the master substrate. The SRPs now function as diffraction gratings on the SPR sensor hips. One or more sensing domains are disposed on the surface of the SPR sensor chip, to which the input light beam is directed.

Preferable moulded materials for SPR sensor chips are transparent polymers such as: acrylics, polycarbonate, polyetherimide (trade name ULTEM 1000, ULTEM 1010), polystyrene, polyurethane resin, cyclo-olefin-copolymer (trade name TOPAS), probimide 293, XU-218, and polyquinoline.

It is known by a person skilled in the art that polymer materials are moulded at high mould temperatures (typically in the range from 70 degrees to 200 degrees), and after being taken out of the mould and cooled down, they will shrink with an amount of typically 0.2–0.7%. As a consequence or the shrinkage, the grating spacing experienced by the reconstruction wave ($a_{read}$), i.e. the grating spacing on the SPR sensor chip will be reduced by the same amount. When forming the diffractive optical elements according to the method of the present invention, the positions of the object wave and the reference wave are adjusted to compensate for the shrinkage.

What is claimed is:

1. A method of forming a first surface relief pattern adapted to be replicated onto a substantially plane surface of a substantially transparent member to form a first diffractive optical element, said substantially transparent member being adapted to form part of a surface plasmon resonance sensor, the method comprising the steps of providing a master substrate, said master substrate having a substantially plane surface, providing a photosensitive layer of material onto the substantially plane surface of the master substrate, exposing the photosensitive layer to a first and a second wave of electromagnetic radiation so as to expose the photosensitive layer to a first interference pattern generated by a spatial overlap at an intersection between the first and second waves of electromagnetic radiation, wherein the first wave of electromagnetic radiation, at the position of the photosensitive layer, has a first mean propagation vector, and wherein the second wave of electromagnetic radiation, at the position of the photosensitive layer, has a second mean propagation vector, the second mean propagation vector forming an angle to the first mean propagation vector at the intersection between the first and second wave of electromagnetic radiation, wherein the angle between the first and second mean propagation vectors is selected so as to change direction of propagation of an incoming wave of electromagnetic radiation having an incoming mean propagation vector in such a way that the smallest angle between the incoming mean propagation vector and a diffracted mean propagation vector is larger than 40 degrees when said incoming wave of electromagnetic radiation is incident upon the first diffractive optical element replicated in the substantially plane surface of the substantially transparent member.

2. A method according to claim 1, further comprising the steps of rotating the master substrate approximately 180 degrees around a normal to the surface holding the photosensitive layer, forming a second surface relief pattern on the substantially plane surface of the master substrate by exposing the photosensitive layer to the first and second waves of electromagnetic radiation so as to expose the photosensitive layer to a second interference pattern generated by the spatial overlap at the intersection between the first and second waves of electromagnetic radiation, wherein the first wave of electromagnetic radiation, at the position of the photosensitive layer, has a first mean propagation vector, and wherein the second wave of electromagnetic radiation, at the position of the photosensitive layer, has a second mean propagation vector, the second mean propagation vector forming an angle to the first mean propagation vector at the intersection between the first and second wave of electromagnetic radiation, wherein the angle between the first and second mean propagation vectors is selected so as to change direction of propagation of an incoming wave of electromagnetic radiation having an incoming mean propagation vector in such a way that the smallest angle between the incoming mean propagation vector and a diffracted mean propagation vector is larger than 40 degrees when said incoming wave of electromagnetic radiation is incident upon a replication of the second surface relief pattern replicated in the substantially plane surface of the substantially transparent member as a second diffractive optical element.

3. A method according to claim 1, wherein the first and second waves of electromagnetic radiation have substantially the same wavelength.

4. A method according to claim 3, wherein the first and second waves of electromagnetic radiation are emitted by a same light source.

5. A method according to claim 4, wherein the same light source comprises a laser, such as a HeCd laser, a Kr-laser, an excimer laser, or a semiconductor laser.

6. A method according to claim 1, further comprising the step of developing the photosensitive layer.

7. A method according to claim 1, wherein the first wave of electromagnetic radiation forms an object wave, the second wave of electromagnetic radiation forms a reference wave, and wherein the incoming waves of electromagnetic radiation form reconstruction waves.

8. A method according to claim 1, wherein the master substrate constitutes the substantially transparent member.

9. A method according to claim 8, further comprising the step of performing a sacrificial-layer-etch of the photosensitive layer in order to replicate the first and second surface relief pattern(s) into the substantially plane surface of a substantially transparent member.

10. A method according to claim 9, wherein the step of performing a sacrificial-layer-etch of the photosensitive layer is achieved by means of ion-milling, chemically assisted ion-beam etching or reactive ion etching.

11. A method according to claim 2, further comprising the step of forming a negative metal master of the first and second surface relief patterns for further replication of said first and second surface relief patterns.

12. A method according to claim 11, wherein the metal master is a nickel master.

13. A method according to claim 11, further comprising the step of replicating the first and second surface relief patterns from the negative metal master using hot embossing.

14. A method according to claim 11, further comprising the step of replicating the first and second surface relief patterns from the negative metal master using injection moulding.

15. A method according to claim 11, further comprising the step of replicating the first and second surface relief patterns from the negative metal master using injection compression moulding.

16. A method according to claim 8, further comprising the step of providing a metal layer on top of the diffractive optical element(s) replicated from the surface relief pattern(s).

17. A method according to claim 16, wherein the provided metal layer comprises a material selected from the group consisting of aluminium, gold, silver or the like.

18. A coupling element for surface plasmon resonance sensors, said coupling element comprising
    a diffractive optical element comprising a grating structure having a monotonically increasing spacing in a predetermined direction, the diffractive optical element being adapted to diffract an incoming wave of electromagnetic radiation having a first mean propagation vector into a diffracted wave of electromagnetic radiation having a second mean propagation vector,
wherein the diffractive optical element forms part of a surface of a solid and substantially transparent member, and wherein the direction of propagation defined by the second mean propagation vector is different from the direction of propagation defined by the first mean propagation vector in such a way that the smallest angle between the first and second mean propagation vectors is larger than 40 degrees.

19. A coupling element according to claim 18, wherein the grating structure forms a transmission grating structure.

20. A coupling element according to claim 18, wherein the grating structure forms a reflection grating structure.

21. A coupling element according to claim 18, wherein the diffractive optical element is adapted to focus an incoming wave of electromagnetic radiation.

22. A coupling element according to claim 18, wherein the diffractive optical element is adapted to collimate a diverging wave of electromagnetic radiation.

23. A coupling element according to claim 18, wherein the diffractive optical element further comprises one or more calibration marks, said one or more calibration marks being areas with missing grating structures.

24. A method according to claim 1, wherein a focal point of the first wave of electromagnetic radiation and a focal point of the second wave of electromagnetic radiation are positioned according to the following procedure
    expanding to third order in x the expression of a recording grating spacing defined as, $$a_{record}(x) = \frac{\lambda_{record}}{\sin(\theta_1) + \sin(\theta_2)},$$

where x is a direction perpendicular to the lines of the interference pattern, $\lambda_{record}$ is a recording wavelength, $\theta_1$ is the angle of incidence of the first wave of electromagnetic radiation and $\theta_2$ is the angle of incidence of the second wave of electromagnetic radiation,
    expanding to third order in x the expression of reconstruction grating spacing defined as, $$a_{read}(x) = \frac{\lambda_{read}}{n_g(\sin(\theta_0) - \sin(\theta_i))},$$

where $\lambda_{read}$ is a reconstruction vacuum wavelength, $n_g$ is a refractive index of the substantially transparent member, $\theta_i$ is the angle of incidence of the incoming wave of electromagnetic radiation and $\theta_0$ is a diffraction angle of a diffracted wave of electromagnetic radiation, and
    minimizing the expression $$a_{record}(x) - a_{read}(x) = A_0 + A_1(x - x_{centre}) + A_2(x - x_{centre})^2 + A_3(x - x_{centre})^3,$$

with respect to the position of the focal point of the first wave of electromagnetic radiation and the position of the focal point of the second wave of electromagnetic radiation, where $x_{centre}$ is the centre position of the interference pattern, and $A_0$, $A_1$, $A_2$, and $A_3$ are the differences between the first, second, third and fourth expansion coefficients of $a_{record}(x)$ and $a_{read}(x)$, respectively.

* * * * *